(12) United States Patent
Burns et al.

(10) Patent No.: US 6,440,388 B1
(45) Date of Patent: *Aug. 27, 2002

(54) METHOD FOR DETECTING CHITIN-CONTAINING ORGANISMS

(75) Inventors: Edward R. Burns, Flushing; Murray Wittner, Larchmont; Fagie Faskowitz, Flushing, all of NY (US)

(73) Assignee: Albert Einstein College of Medicine of Yeshiva University, Bronx, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/193,923

(22) Filed: Nov. 17, 1998

Related U.S. Application Data

(63) Continuation-in-part of application No. 08/971,384, filed on Nov. 17, 1997, now Pat. No. 5,997,846.

(51) Int. Cl.$^7$ .......................... A61B 10/00; A61B 5/00; A61B 8/00

(52) U.S. Cl. .................. 424/9.6; 424/1.11; 424/9.1; 424/9.8; 536/20

(58) Field of Search .................... 424/1.11, 9.1, 424/9.2, 9.3, 9.4, 9.5, 9.6, 9.7, 9.8; 206/223, 569, 570; 536/20

(56) References Cited

U.S. PATENT DOCUMENTS

| 4,380,790 A | 4/1983 | Saferstein |
| 5,004,699 A | 4/1991 | Winters |
| 5,292,504 A | 3/1994 | Cardin et al. |
| 5,353,803 A | 10/1994 | Cerra |
| 5,547,665 A | 8/1996 | Upton |
| 5,561,051 A | 10/1996 | Silverman |
| 5,587,292 A | 12/1996 | Laine et al. |
| 5,997,846 A | * 12/1999 | Burns et al. ................ 424/9.6 |
| 5,997,847 A | 12/1999 | Spiesel ...................... 424/9.6 |

FOREIGN PATENT DOCUMENTS

| WO | WO 9217786 A | 10/1992 |

OTHER PUBLICATIONS

J. Vavra, et al., Staining of Microsporidian Spores by Optical Brighteners with remarks on the use of Brighteners for the Diagnosis of AIDS Associated Human Microsporidioses, *Folia Parasitologica*, pp 267–272 (1993).

Sutphin, et al., Improved detection of Oculomycoses using induced fluorescence with celluflor, *Opthamology*, 416–417, (1986).

Conteas, et al., Fluorescence Techniques for Diagnosing Intestinal Microsporidiosis in Stool, Enteric Fluid and Biopsy Specimens from Acquired Immunodeficiency Syndrome patients with chronic diarrhea, *Arch Pathol. Lab. Med.*, : vol. 120, Sep. 1996.

Hegeage, Jr., et al., Use of Calcofluor White in Clinical Mycology, *Laboratory Medicine*, vol. 15, No. 2, Feb. 1984, pp 109–112.

Hoffgen, et al., The use of Funguigual A as a fluorescent dye in Medical Mycology, *Aktuel–Dermatol.*, vol. 15 No. 7, 1989, pp 216–20 (English Abstract only).

Hejtmanek, et al., Fluorescence Microscopy detection of Mycopathogens using Rylux BSU, *Cesk Patol*, 1989, Nov. 25(4) : 244–50 (English Abstract only).

Raclavsky, et al., Quantitative determination of yeast in sputum—a direct microscopy method, *Cesk Epidemiol Mikrobiol Immunol*, 1989 May; 38(3) : 161–6 (English Abstract only).

Costello, "This Gizmo Could Just Bring Out a Little Compulsiveness in Us All," Wall Street Journal, Oct. 13, 1998, Section B, p. 1.

Osswald, et al., Quantitative fluorometric analysis of plant and microbial chitosanases, *Anal. Biochem.* Jul. 1992; 204(1): 40–6.

Carrano, et al., Dansyl N–acetyl glucosamine as a precursor of fluorescent chitin: a method to detect fungal cell wall inhibitors, *J. Antibiot* (Tokyo) Feb. 1997; 50(2) : 177–9.

(List continued on next page.)

*Primary Examiner*—Dameron L. Jones
(74) *Attorney, Agent, or Firm*—Amster, Rothstein & Ebenstein

(57) ABSTRACT

The present invention provides a method for detecting chitin-containing organisms on an area of a person of animal by contacting the particular area with a dye that is capable of binding or conjugating to chitin and emitting fluorescence upon exposure to light. If a chitin-containing organism is present in the treated area, the chitin of the organism will bind or conjugate the dye and, upon exposure to light, the chitin-containing organisms may be visualized and removed. Also provided by the present invention are solutions and suspensions that contain a dye capable of binding or conjugating to a chitin-containing organism and emitting fluorescence upon exposure to light. The solutions and suspensions provided herein may be in the form of a shampoo, cream, lotion or detergent for the detection of chitin-containing organisms present in body hair, on the skin, clothing or the fur of animals. The solutions and suspensions may also be in a form suitable for spraying on clothes, as well as on the hair, skin and fur. Further provided by the present invention are kits comprising a solution or suspension that contains a dye capable of binding or conjugating to a chitin-containing organism and a source of light that emits a wavelength capable of exciting fluorescence from the chitin-bound or chitin-conjugated dye.

14 Claims, No Drawings

OTHER PUBLICATIONS

Trudel, et al., Detection of chitin deacetylase activity after polyaciylamide gel electrophoresis, *Anal. Biochem.* Sep. 1990; 189(2) : 249–53.

Borg–Von Zepelin, Fluorescence assay for the detection of adherent candida yeasts to target cells in microtest plates, *Mycoses* Sep.–Oct. 1995; 38 (9–10) : 339–47.

Sromova, et al., Fluorescence—microscopic visualization of chitin structures in egg shells of *Ascaris lumbricoides, Folia Parasitol* (Praha) 1987; 34(4) : 367–8.

Dox, et al., (1993) The Harper Collins Illustrated Medical Dictionary, pp 96, 177, 253, 276, 336, 480, 531.

* cited by examiner

METHOD FOR DETECTING CHITIN-CONTAINING ORGANISMS

CROSS-REFERENCE TO RELATED APPLICATIONS

This is a continuation-in-part of application Ser. No. 08/971,384, filed Nov. 17, 1997, now U.S. Pat. No. 5,997,846, the contents of which are hereby incorporated by reference in their entirety.

BACKGROUND OF THE INVENTION

Numerous human and animal diseases are caused by the bite of or infestation by arthropods. Arthropods include insects such as lice and arachnids such as mites and ticks. Because of the small size of these creatures and their larvae, it is often difficult to detect their presence on people or their pets.

Human pediculosis, or lice, is caused by infestation of the head, body, or pubic area by the arthropods *Pediculus capitus, Pediculus humanus, Pediculus corporis* or *Phithirus pubis*, respectively. Head lice lay eggs, called nits or louse eggs, on the hair of the head, and the nits eventually hatch into mature forms. Body lice lay their eggs in warm moist skin crease areas. Treatment is with shampoos, creams and lotions containing various insecticides such as lindane, Malathion, or permethrin. Following treatment, the residual nits must be removed by careful examination of the affected hair or clothing and mechanical removal. The shampoo treatment does not remove nits which tenaciously adhere to hair.

Most pre-schools and elementary schools in the U.S. have periodic checks of their students for lice to limit infections. The child's head is checked for the presence of either nits or lice, and if found, the child is sent home for treatment. After treatment, the child is rechecked in school. Often, however, a successfully treated child will have residual nits that were missed and not removed. This usually results from an inability to see the small (0.8 mm×0.3 mm) eggs that blend in well with hair, especially light hair. For the untrained observer, it is often difficult to differentiate nits from exfoliated scalp skin (dandruff). This may lead to further embarrassment of a child who might have been treated but is sent home again after finding residual nits.

U.S. Pat. No. 4,830,790, issued Apr. 19, 1993 to Saferstein, A. for "Multi-Function Light Device" describes a source of blacklight blue light for the detection of nits and adult lice. Since autofluorescence of nits and adult lice is minimal, however, it is still extremely difficult to detect nits and adult lice in hair and clothing.

Lyme disease or erythema chronicum migrans is a multi system disease affecting the skin joints and central nervous system caused by the organism *Borrelia burgdorefi*. The disease is contracted by the bite of the deer tick *Ixodes scapularis* which secretes the Borrelia organism in its saliva when it feeds off the human host. Other tick vectors found to be associated with the Borrelia organism are *Ixodes pacificus*, found in the west, *I. ricinus*, found in Europe, and *I. persulcatus*, found in Asia. Rocky Mountain spotted fever is an acute rickettsial disease that is transmitted by the bite of a wood tick, *Dermacentor andersoni*. Rapid removal of the deer and wood ticks after attachment could prevent the transmission of the Borrelia and Dermacentor organisms and thus prevent Lyme disease or Rocky Mountain spotted fever, but is often difficult since the attachment and bite of the tick are most often not seen or felt by the host.

Other organisms that are small in size and thus difficult to detect are mites, such as chiggers. These organisms also cause human disease. Accordingly, a need remains for an effective and expedient method of detecting small organisms, such as lice, nits, mites, ticks, and fungi.

SUMMARY OF THE INVENTION

The present invention provides a precise and efficient method of detecting chitin-containing organisms such as lice, nits, mites, ticks, and fungal infections of the skin. The method provided herein enables a quick and accurate detection of chitin-containing organisms on areas such as the hair, skin and clothing of humans and the fur and skin of animals.

The method provided by the present invention involves the steps of treating the hair, scalp, skin, or clothing with a dye that fluoresces when exposed to ultraviolet or visible light. If a chitin-containing organism is present in the treated area, the chitin of the organism will bind the dye. The area is then exposed to ultraviolet light and the chitin-containing organism fluoresces and can be visualized and removed.

The present invention also provides solutions and suspensions that contain a dye capable of binding to a chitin-containing organism in an amount effective to bind to a chitin-containing organism and emit fluorescence upon exposure to light. The solutions and suspensions provided herein may be in the form of a shampoo, cream, lotion or detergent for the detection of chitin-containing organisms present in body hair, on the skin, clothing or the fur of animals. The solutions and suspensions may also be in a form suitable for spraying on clothes, as well as on the hair, skin and fur.

The present invention also provides a kit comprising a solution or suspension that contains a dye capable of binding to a chitin-containing organism and a source of light that emits a wavelength capable of exciting fluorescence from the chitin-bound or chitin-conjugated dye.

The method provided herein is extremely useful for the detection of nits, which are difficult to see with the naked eye. Another useful application of the novel method of the present invention is the detection of ticks, such as the deer tick which carries Borrelia, the organism which causes Lyme disease. Deer ticks are extremely small, and must be immediately removed from the site of attachment in order to prevent transmission of the Borrelia organism.

Additional objects of the invention will be apparent from the description which follows.

DETAILED DESCRIPTION OF THE INVENTION

The present invention provides a precise and efficient method of detection of chitin-containing organisms. The method provided by the present invention allows for the visualization of chitin-containing organisms by treating an area of a human or animal with a dye that renders the chitin-containing organism fluorescent when exposed to ultraviolet or visible light. Chitin is a nitrogen containing polysaccharide within a class of polymers of N-acetylglucosamine present in the covering layer of insects and in the cell walls of many fungi. In particular, chitin is a major component of arthropod shells and the cell walls of lice, nits, mites, ticks, and fungi. Chitin is suitable for staining and is unique to the arthropod while absent from humans and other mammals.

The present invention provides a method for detecting chitin-containing organisms. The novel method provided herein employs a dye that stains chitin by binding or conjugating to chitin and fluoresces when exposed to ultraviolet or visible light. The particular dye is capable of fluorescing only when bound or conjugated to chitin. The dye is placed in contact with the area to be tested, and the chitin-containing organisms that come into contact with the dye will absorb the dye and fluoresce upon exposure to ultraviolet or visible light. The organism can then be easily located and removed.

The preferred dyes employed in the method of the present invention are those that both bind or conjugate chitin and fluoresce in ultraviolet or visible light. Non-limiting examples of dyes that bind or conjugate chitin and fluoresce in ultraviolet or visible light include calcofluor white, Uvitex 3B (distyryl biphenyl fluorescent whitening agent), Rylux BA, Rylux BSU (1,4-benzenedisulfonic acid-2,2'-[ethyleneidylbis[(3-sulpho-4,1-phenylene)imino[6-bis (2-hydroxyethyl)amino]-1,3,5-trihexasodium salt) (Ostacolor, Pardubice, Czech Republic) and Blankophor (disodium 4,4'-bis{(4-anilino)-6-morpholino-1,3,5-triazin-2-yl) amino}stilbene-2,2'-disulphonate)_(Bayer). Calcofluor white and Uvitex 3B (distyryl biphenyl fluorescent whitening agent) a colorlees dyes that fluoresce brightly on exposure to long wave ultraviolet light and short wavelengts visible light. Calcofluor white may be obtained as fluorescent brightener 28 (Tinopal UNPA-GX) in the salt or the free acid form (Sigma Chemical Co., St. Louis, Mo.) or calcofluor white M2R (Poly-sciences, Inc., Warrington, Pa., or Sigma Chemical Co., St. Louis, Mo.). A preferred concentration of calcofluor white or Uvitex B (distyryl biphenyl fluorescent whitening agent) for use in the direct application to the skin of a human or animal is 1% of the dye dissolved in distilled water, although effective concentrations may be anywhere between 0.01%–5%, 0.01–1.5%, 0.005–2&, 0.75–1.3% or 0.01–10%.

Examples of arthropods that can be detected using the method provided herein include lice, ticks, and mites, such as chiggers. Examples of lice that may be detected include head lice, body lice, and pubic or crab lice. Head lice, caused by the infestation of *Pediculus capitus*, is the most common variety to appear on the head and scalp. Body lice, cause by the infestation of *Pediculus humanus*, are usually found on clothing. *Phithirus pubis* usually infests pubic hair, but can also be found on the eyelashes, eyebrows, mustache, or beard. Also detectable by the method of the present invention are nits, or louse eggs. Head lice and pubic lice most commonly attach their eggs to hair, while body lice attach their eggs to clothing fibers. These areas can be treated using the method of the present invention to locate and remove nits.

The method of the present invention also detects fungal infections caused by organisms such as blastomyces, aspergillus, cryptococcus and candida. Also detectable by the method described herein are infections caused by dermatophytic fungi that manifest as ringworm. Examples of fungal infections that are detectable using the novel method of the present invention are tinea capitis, a fungal infection of the scalp, caused by Microsporum and Trichophyton species; *tinea corporis*, a fungal infection of the body, caused by Epidermophyton, Microsporum and Trichophyton species; *tinea pedis*, otherwise known as athlete's foot, caused by Epidermophyton and Trichophyton species; *tinea unguium*, a fungal infection of the nails, caused by Trichophyton species; and *tinea cruris*, a fungal infection of the groin, caused by Trichophyton and Epidermophyton species. Also detectable by the method of the present invention is the ringworm caused by *Microsporum canis*, a fungus which commonly infects dogs and cats.

The present invention further provides a solution or suspension comprising a dye capable of binding or conjugating to a chitin-containing organism in an amount effective to bind or conjugate to a chitin-containing organism and emit fluorescence upon exposure to light. The solution or suspension provided herein may contain, for example, a dye such as calcofluor white or Uvitex 3B (distyryl biphenyl fluorescent whitening agent). The solution or suspension may comprise about 0.01% to 10% of the dye, with the preferred amount being about 1%. The solution or suspension of the present invention may be in the form of a shampoo, cream, lotion, detergent, or spray. In a preferred embodiment of the invention, the dye is incorporated into a shampoo and nits are visualized with ultraviolet light after shampooing. In another embodiment, the dye is incorporated in a cream or lotion formulation. In a further embodiment of the invention, the colorless dye that fluoresces upon exposure to ultraviolet light is contained in a solution or suspension which is suitable for spraying on hair, skin, clothing and the fur of animals for the visualization of organisms upon exposure to ultraviolated light. Since the colorless dye fluoresces only when bound or conjugated to chitin, the solution does not need to be removed from the surrounding area to visualize the fluorescing tick. The fluorescent ticks, mites, nits, or other organism can then be pinpointed and removed. This embodiment of the invention is extremely useful for visualizing organisms that are difficult to detect because of their small size, such as ticks, lice, and mites. This embodiment of the invention is particularly useful for the visualization of the deer tick, *Ixodes scapularis*, which carries *Borrelia burgdorefi*, the causative agent of Lyme disease. A further, very practical use of this embodiment is the visualization of nits for rapid and accurate detection. For example, the spray solution or suspension can be used to quickly detect the presence of lice and their eggs on hair and clothing as part of screening programs in schools, camps, physician's offices, pediatric clinics and emergency rooms. The spray solution or suspension may also be used to detect chitin-containing organisms on furniture, bedding, and grooming utensils, such as brushes and combs. The spray solution or suspension of the present invention may also be employed for the detection of ticks, mites, and fungi on the fur and skin of animals, such as dogs and cats.

Further provided by the present invention is a kit comprising a suspension containing a dye capable of binding or conjugating to a chitin-containing organism in an amount effective to bind or conjugate to a chitin-containing organism and emit fluorescence upon exposure to light, and a source of light that emits a wavelength capable of exciting fluorescence from the chitin-bound or chitin-conjugated dye.

The source of light that emits a wavelength capable of exciting fluorescence from the chitin-bound or chitin-conjugated dye may be a source of ultraviolet or visible light. Preferably, the source of light contained in the kit is a source of long wave ultraviolet light or short wave visible light. The dye contained in the solution or suspension which is a part of the kit provided by the present invention is calcofluor white, Uvitex 3B (distyryl biphenyl fluorescent whitening agent), Rylux BA, Rylux BSU (1,4-benzenedisulfonic acid-2,2'-[ethyleneidylbis[(3-sulpho-4,1-phenylene)imino[6-bis(2-hydroxyethyl)amino]-1,3,5-trihexasodium salt) or Blankophor (disodium 4,4'-bis{(4-anilino-6-morpholino-1,3,5-triazin-2-yl)amino}stilbene-2, 2'-disulphonate).

The present invention is described in the following Experimental Details Section, which is set forth to aid in an understanding of the invention, and should not be construed to limit in any way the invention as defined in the claims which follow thereafter.

Experimental Details Section

Visualizing Nits

Human hair with attached *P. capitis* nits obtained as a waste product after barbering were obtained and dipped into a 1% solution of calcofluor white for two minutes. The hair was removed and examined wet under UV light. The nits were clearly seen as brightly fluorescent white ovoid bodies against a non-fluorescent black background. Identification was easy, specific, and totally unambiguous.

Toxicity Data

The 1% solution was also spread on the dorsum of four hands of volunteers and allowed to remain continuously for 12 hours before being washed off. The solution caused no physical sensation and did not provoke any physical reactions such as pruritus, erythema, induration or discoloration.

Visualizing Deer Ticks

Use as a visualizing agent for deer ticks was investigated as well. Live deer ticks were gathered from a wooded area in Westchester County, N.Y. and sprayed with a 1% solution of Calcofluor white. The ticks were placed on a white cotton sheet and exposed to long range UV light from a portable UV lamp. The ticks were easily visualized as brightly fluorescent objects against a dark background.

In order to determine whether deer ticks and related arthropods exhibit autofluorescence, several deer ticks were collected on a white cotton sheet and subjected to exposure to long range ultraviolet light. There was no fluorescence demonstrated. The addition of a subsequent spray of Calcofluor white on the deer ticks with a follow up exposure to ultraviolet light then showed intense fluorescence.

Commercial Applications

It is estimated that millions of children are treated and examined for head lice each year. Untold millions of people a year are exposed to deer ticks and would be a likely group of people who would want to screen themselves for deer tick bites.

In addition, countless pet dogs and cats are infected with ringworm caused by *Microsporum canis* which also contains chitin.

While the foregoing invention has been described in some detail for purposes of clarity and understanding, it will be appreciated by one skilled in the art from a reading of the disclosure that various changes in form and detail can be made without departing from the true scope of the invention in the appended claims.

What is claimed is:

1. A solution or suspension comprising a dye that binds to a chitin-containing organism, the dye being present in an amount effective to bind the chitin-containing organism and emit fluorescence upon exposure to light, wherein the solution or suspension is formulated in a shampoo, lotion, cream, detergent or spray and, when applied to skin, hair, fur or clothing, the solution or suspension renders an arthropod detectable wherein the dye is calcofluor white.

2. The solution or suspension of claim 1, wherein the solution or suspension is formulated in a shampoo.

3. The solution or suspension of claim 1, wherein the solution or suspension is formulated in a lotion.

4. The solution or suspension of claim 1, wherein the solution or suspension is formulated in a cream.

5. The solution or suspension of claim 1, wherein the solution or suspension is formulated in a detergent.

6. The solution or suspension of claim 1, wherein the solution or suspension is formulated in a spray.

7. The solution or suspension of claim 1, wherein the dye comprises 0.01–5% of the solution or suspension.

8. A solution or suspension comprising a dye that binds to a chitin-containing organism, the dye being present in an amount effective to bind the chitin-containing organism and emit fluorescence upon exposure to light, wherein the solution or suspension is formulated in a shampoo, lotion, cream, detergent or spray and, when applied to skin, hair, fur or clothing, the solution or suspension renders an arthropod detectable, wherein the dye is distyryl biphenyl fluorescent whitening agent.

9. The solution or suspension of claim 8, wherein the solution or suspension is formulated in a shampoo.

10. The solution or suspension of claim 8, wherein the solution or suspension is formulated in a lotion.

11. The solution or suspension of claim 8, wherein the solution or suspension is formulated in a cream.

12. The solution or suspension of claim 8, wherein the solution or suspension is formulated in a detergent.

13. The solution or suspension of claim 8, wherein the solution or suspension is formulated in a spray.

14. The solution or suspension of claim 8, wherein the dye comprises 0.01–5% of the solution or suspension.

* * * * *